(12) United States Patent
Chan et al.

(10) Patent No.: US 6,577,888 B1
(45) Date of Patent: Jun. 10, 2003

(54) SLIDING-DOME AND SPLIT-TOP MRI RADIO FREQUENCY QUADRATURE ARRAY COIL SYSTEM

(75) Inventors: Pei Hsuon Chan, Aurora, OH (US); Matthias Gyori, Hudson, OH (US); Mark Xueming Zou, Aurora, OH (US)

(73) Assignee: USA Instruments, Inc., Aurora, OH (US)

( * ) Notice: Subject to any disclaimer, the term of this patent is extended or adjusted under 35 U.S.C. 154(b) by 188 days.

(21) Appl. No.: 09/676,225

(22) Filed: Sep. 29, 2000

(51) Int. Cl.[7] .............................. A61B 5/055; G01V 3/00
(52) U.S. Cl. ........................................ 600/422; 324/318
(58) Field of Search ................................. 600/421, 422; 324/309, 318

(56) References Cited

U.S. PATENT DOCUMENTS

| | | | | |
|---|---|---|---|---|
| 4,692,705 A | * | 9/1987 | Hayes | 324/318 |
| 4,825,162 A | * | 4/1989 | Roemer et al. | 324/318 |
| 5,274,332 A | * | 12/1993 | Jaskolski et al. | 324/318 |
| 5,361,765 A | * | 11/1994 | Herliby et al. | |
| 5,379,767 A | * | 1/1995 | Derby et al. | |
| 5,517,120 A | * | 5/1996 | Misic et al. | 324/318 |
| 5,543,711 A | * | 8/1996 | Srinivasan et al. | 324/318 |
| 5,602,479 A | * | 2/1997 | Srinivasan et al. | 324/318 |
| 5,664,568 A | * | 9/1997 | Srinivasan et al. | |
| 6,037,773 A | * | 3/2000 | Mitsumata et al. | 324/318 |
| 6,150,816 A | * | 11/2000 | Srinivasan | 324/318 |
| 6,356,081 B1 | * | 3/2002 | Misic | 324/318 |
| 6,441,612 B1 | * | 8/2002 | Shimo et al. | 324/309 |

* cited by examiner

Primary Examiner—Shawna J Shaw
(74) Attorney, Agent, or Firm—Pearne & Gordon LLP (57) ABSTRACT

An MRI array coil system for neurovascular and spine imaging of a human includes a neck coil having a split top; a dome-like head coil having a dome region, the head coil being slidable between a closed position adjacent to the neck coil and an open position spaced away from the neck coil; a posterior torso coil attached to the neck coil; and an anterior torso coil adapted to cooperate with the posterior coil.

5 Claims, 6 Drawing Sheets

SLIDING-DOME AND SPLIT-TOP MRI RADIO FREQUENCY QUADRATURE ARRAY COIL SYSTEM

BACKGROUND OF THE INVENTION

This invention relates to magnetic resonance imaging (MRI) systems, and particularly to the radio-frequency (RF) coils used in such systems.

MRI utilizes hydrogen nuclear spins of the water molecules in organic tissue, which are polarized by a strong, uniform, static magnetic field of a magnet (named $B_0$—the main magnetic field in MRI physics). The magnetically polarized nuclear spins generate magnetic moments in the tissue. The magnetic moments point in the direction of the main magnetic field in a steady state, and produce no useful information if they are not disturbed by any excitation.

The generation of a nuclear magnetic resonance (NMR) signal for MRI data acquisition is accomplished by exciting the magnetic moments with a uniform RF magnetic field (named $B_1$—the excitation field). The $B_1$ field is produced in the imaging region of interest by an RF transmit coil which is driven by a computer-controlled RF transmitter with a power amplifier. During excitation, the nuclear spin system absorbs magnetic energy, and it's magnetic moments precess around the direction of the main magnetic field. After excitation, the precessing magnetic moments will go through a process of free induction decay, releasing their absorbed energy and returning to the steady state. During free induction decay, NMR signals are detected by the use of a receive RF coil, which is placed in the vicinity of the excited volume of the tissue. The NMR signal is the secondary electrical voltage (or current) in the receive RF coil that has been induced by the precessing magnetic moments of the tissue. The receive RF coil can be either the transmit coil itself, or an independent receive-only RF coil. The NMR signal is used for producing MR images by using additional pulsed magnetic gradient fields, which are generated by gradient coils integrated inside the main magnet system. The gradient fields are used to spatially encode the signals and selectively excite a specific volume of the human body. There are usually three sets of gradient coils in a standard MRI system, which generate magnetic fields in the same direction of the main magnetic field, varying linearly in the imaging volume.

In MRI, it is desirable for the excitation and reception to be spatially uniform in the imaging volume for better image uniformity. In a standard MRI system, the best excitation field homogeneity is usually obtained by using a whole-body volume RF coil for transmission. The whole-body transmit coil is the largest RF coil in the system. A large coil, however, produces lower signal-to-noise ratio (SNR or S/N) if it is also used for reception, mainly because of its greater distance from the signal-generating tissue being imaged. Since a high signal-to-noise ratio is desirable in MRI, special-purpose coils are used for reception to enhance the S/N ratio from the tissue volume of interest.

It is desirable for specialty RF coil to have the following functional properties: high S/N ratio, good uniformity, high unloaded quality factor (Q) of the resonance circuit, and high ratio of the unloaded to loaded Q factors. In addition, the coil device may be mechanically designed to facilitate tissue sample (e.g., human body, animal, or other organic tissue) handling and comfort, and to provide a protective barrier between the tissue and the RF electronics. Another way to increase the SNR is by quadrature reception. In this method, NMR signals are detected in two orthogonal directions, which are in the transverse plane or perpendicular to the main magnetic field. The two signals are detected by two independent individual coils which cover the same volume of interest. With quadrature reception, the SNR can be increased by up to $\sqrt{2}$ over that of the individual linear coils.

In MRI and Magnetic Resonance Angiography (MRA), a neurovascular RF coil is used head, neck/c-spine and vascular imaging without repositioning the sample (e.g., a human patient). The coverage of a neurovascular coil, depending on the usable imaging volume (e.g., a sphere of 45 to 50 cm in diameter), may be about 48 cm (from the top of the head to the aortic arch). It is desirable for the performance, i.e., signal-to-noise ratio (SNR) and image uniformity, of a neurovascular coil to be comparable to a conventional head coil for head imaging and to a stand-alone neck coil for neck/c-spine imaging. For vascular imaging, it is desirable for a neurovascular coil to be able to provide homogeneous images for coverage of the blood vessels from the circle of Willis to the aortic arch for most of the patient population.

To cover the head and neck with a single RF coil, an asymmetric birdcage coil design has been used. In this design, the anterior and posterior parts of a conventional birdcage (Hayes, U.S. Pat. No. 4,692,705) head coil are extended further over the neck and chest regions to cover these regions. The asymmetric birdcage coil is operated in quadrature mode for head and neck imaging.

To further extend the coverage to the aortic arch, a quadrature RF coil has also been implemented by (Misic, et al., U.S. Pat. No. 5,517,120) for neurovascular imaging and spectroscopy of the human anatomy. This neurovascular coil utilizes multiple horizontal conductors and end conductors to distribute the current such that two orthogonal magnetic modes, i.e., one horizontal field and one vertical field, are created by the coil to achieve the quadrature detection of magnetic resonance signal. Mechanically, the neurovascular coil is separated into two shells: an upper shell for the anterior conductors and a lower shell for the posterior conductors. These two shells are connected by a hinge at the middle of the top end of the head coil mechanical housing.

The development of array coil technology (Roemer, et al., U.S. Pat. No. 4,825,162) allows one to image a large field-of-view (FOV) while maintaining the SNR characteristic of a small and conformal coil. Using this concept, a two channel (four linear coils) volume array coil for magnetic resonance angiography of the head and neck has been built. The first channel is a four bar quadrature head coil consisting of two linear coils. Two Helmholtz type coils form the second channel for covering the neck and chest. The two Helmholtz type coils are arranged such that the magnetic fields generated by them are diagonally oriented and perpendicular to each other (i.e., a quadrature coil pair). The quadrature neck coil is attached to the quadrature head coil. Each of the two Helmholtz type neck coils overlaps with the head coil to minimize the inductive coupling between the head and neck coils, i.e., the neck coils are critically coupled to the head coil, to reduce the noise correlation caused by the cross-talk between the head and the neck coils.

A split-top, four channel, birdcage type array coil has also been developed (Srinvasan, et al., U.S. Pat. No. 5,664,568; U.S. Pat. No. 5,602,479) for head, neck and vascular imaging. This split-top head and neck coil consists of a birdcage head coil and two distributed type (flat birdcage type) coils: one for the anterior neck-torso and the other for the posterior neck-torso. The quadrature signal obtained with the head coil is separated into two channel. The anterior and posterior neck-torso coils form the other two channels. The housing of the head and neck coil is divided into two parts: the lower housing for the posterior one half of the head coil and the posterior neck-torso coil and the upper housing for the anterior one half of the head coil and the anterior neck-torso coil. The upper housing is removable, i.e., a split top. The upper housing is secured to the lower housing with a latch during imaging. The inductive coupling between the neck-torso coils and the head coil is minimized by overlapping the neck-torso coils with the head coil.

It is known that significant gains in SNR (about 30%) can be achieved by using two short overlapping decoupled birdcage coils to cover the whole field-of-view compared to a single birdcage coil covering the same field-of-view. Converging the horizontal bars of the short birdcage coil, that covers the top part of the head, to a smaller endring, a further improvement in the SNR (about 40%) and better image homogeneity have been realized.

Employing an asymmetric birdcage head and neck coil enlarges the size of a conventional birdcage head coil to cover the neck region. This compromises the performance (i.e., SNR) of the head-section of the asymmetric birdcage coil as compared to a conventional birdcage head coil. The anterior neck-torso coil section is far away from a patient's chest (for most of the patient population) and its shape is not optimized to fit the human neck-chest contour. Thus, the performance of the neck-torso section of the asymmetric birdcage coil is lower than that of its head section. The SNR drops quickly from the neck region to the chest region. This limits the coverage of the asymmetric birdcage coil to only the head and neck, not the aortic arch.

The quadrature neurovascular coil design, like the asymmetric birdcage coil design mentioned above, also uses a big single coil for covering the entire FOV from the top of the head to the aortic arch. The anterior chest coil section is also attached to the anterior head coil and far away from a patient's chest (for most of the patient population). Therefore, this neurovascular coil also has the same weaknesses as those of the above asymmetric birdcage coil, for example: lower SNR for the head imaging as compared to a conventional quadrature head coil and imaging non-uniformity of the chest region due to the quick SNR drop-off in this region.

The coverage of the two channel quadrature (four linear coil elements) volume array coil is only for the head and neck but not for the aortic arch. The quadrature head coil generates magnetic fields in both the horizontal and vertical directions but the quadrature neck coil produces magnetic fields in the diagonal directions. In other words, the $B_1$ fields (the magnetic fields generated by MRI RF coil) of the head region and the $B_1$ fields of the neck region are not quadrature (i.e., not perpendicular to each other). Thus, the each of the two linear neck coil elements has to be critically coupled to the two linear head coil elements simultaneously. This increases the complication of isolating the neck coil from the head coil and makes it less robust for manufacture.

The anterior neck-torso coil of the four channel vascular coil is also attached to the anterior head coil and far away from a patient's chest (for most of the patient population). In addition, both the anterior and posterior neck-torso coils are linear coils. These result in insufficient sensitivity/penetration in imaging the chest region and therefore, cause substantial image non-uniformity for vascular imaging from the circle of Willis to the aortic arch. Image intensity correction is needed to improve the image homogeneity. The decoupling of the multiple modes (i.e., multiple NMR frequencies) birdcage type anterior and posterior neck-torso coils from the multiple modes birdcage head coil is much more difficult than that between two single mode linear coils. The big split-top housing, when being moved toward a patient's face, may cause some patients to feel threatened.

The major disadvantages of the above designs are 1) lower SNR for head imaging as compared to a conventional quadrature head coil, 2) for large field-of-view imaging, i.e., from the top of the head to the aortic arch, the image uniformity is not good due to rapid signal drop-off at the chest region and 3) lack of a capability of being used as a neck-only/c-spine-only coil.

The optimized birdcage array coils can only cover the head and part of the neck but not the aortic arch. Furthermore, the multiple modes birdcage coil design makes it more difficult to decouple the array coils from each other. This reduces the flexibility of adding more coil elements to the birdcage array coils to extend its coverage to the aortic arch.

SUMMARY OF THE INVENTION

An MRI array coil system for neurovascular and spine imaging of a human includes a neck coil having a split top; a dome-like head coil having a dome region, the head coil being slidable between a closed position adjacent to the neck coil and an open position spaced away from the neck coil; a posterior torso coil attached to the neck coil; and an anterior torso coil adapted to cooperate with the posterior coil.

DESCRIPTION OF THE EMBODIMENTS

Figure 1:
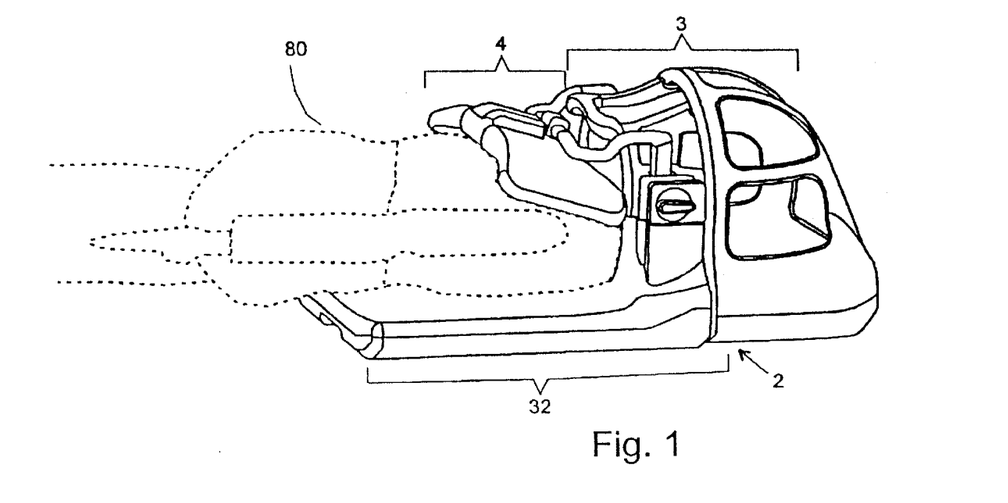
FIG. 1 is a perspective view of a system according. to the invention in a typical operating position.
Figure 2:
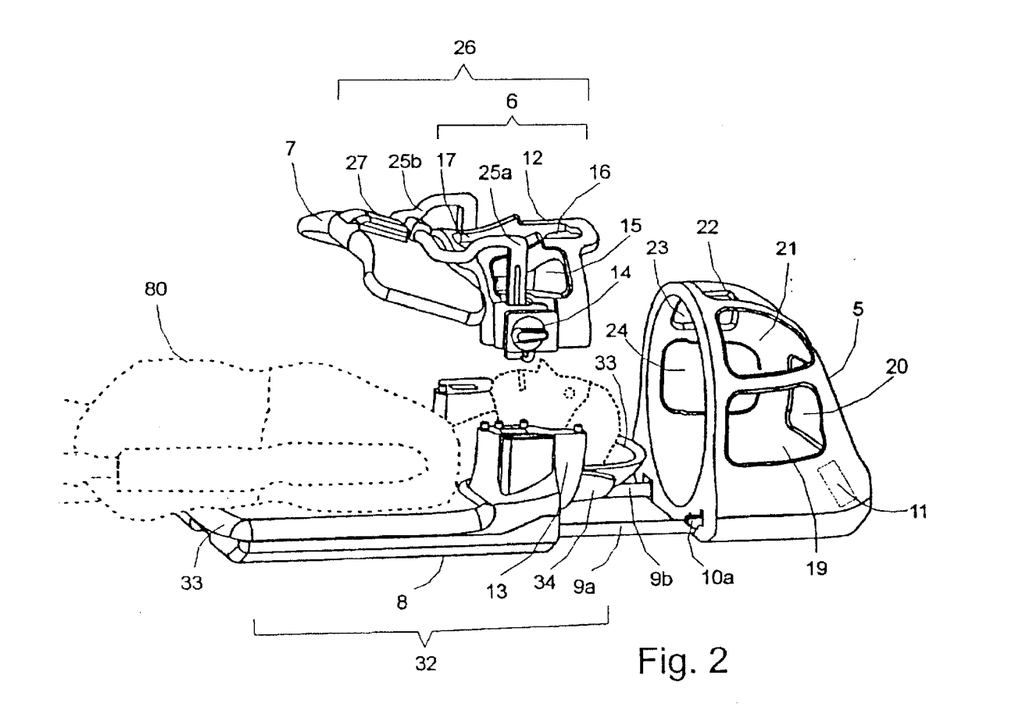
FIG. 2 is a perspective view of a system according to the invention in an open position for patient positioning.

Referring to FIGS. 1 and 2, an MRI RF quadrature array coil system 2 includes two sections: a head-neck section 3 and a torso section 4. The head-neck section 3, includes a sliding-dome head coil 5 and a split-top neck coil 6. The section 3 covers the head and the superior part of the neck of a human patient 80. The torso section 4, includes an anterior torso coil 7 and a posterior torso coil 8. The torso section 4 covers the inferior part of the neck and the torso of a human patient 80.

Figure 3:
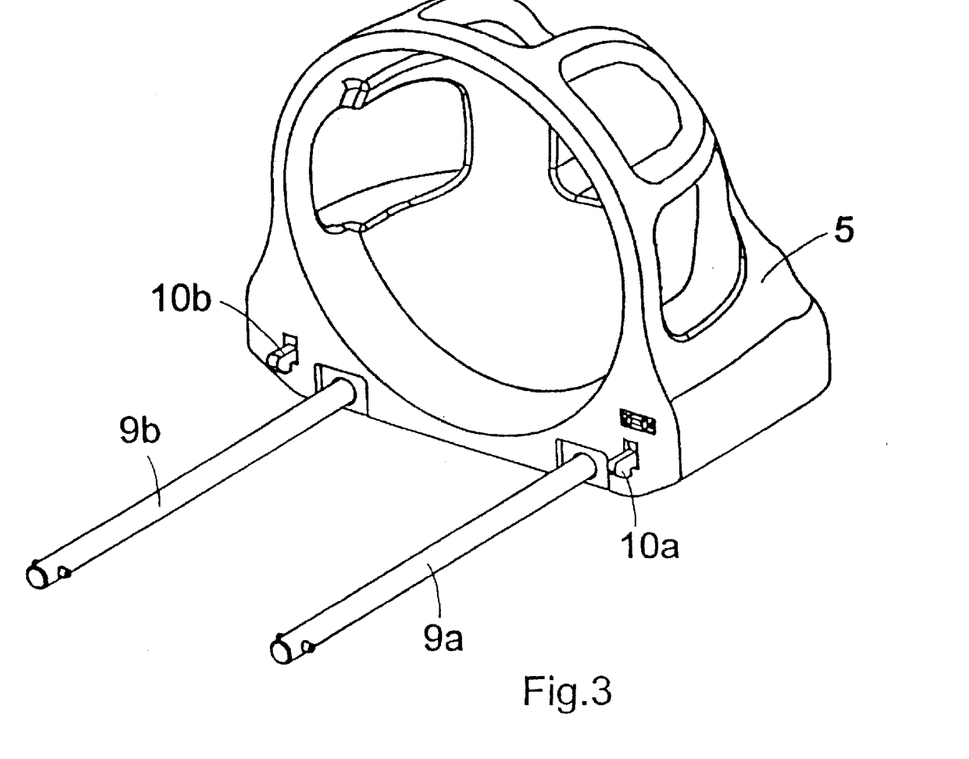
FIG. 3 is a perspective view of a sliding-dome head coil according to the invention.

The sliding-dome head coil 5 can be slid on a pair of sliding tracks 9a, 9b (see FIG. 3). Two latches 10a, 10b on the sliding-dome head coil 5 are used to lock the sliding-dome head coil 5 in position when it is fully engaged with the split-top neck coil 6, as shown in FIG. 1. A push button 11 is used to release the latches 10a, 10b via an unshown mechanism to unlock the sliding-dome head coil 5 allowing the sliding-dome head coil 5 to slide to an open position as shown in FIG. 2. The tracks 9a, 9b glide on unshown sleeves or other bearings in the head-neck section 3.

The split-top neck coil 6 can be separated, at the middle of the neck coil housing, into an anterior neck coil 12 and a posterior neck coil 13. An anterior torso coil 7 is removably attachable to the anterior neck coil 12 as more fully described below. The anterior neck coil 12, with or without the anterior torso coil 7 attached to it, is removable and is securable to the posterior neck coil housing 13 with a pair of latches 14 during imaging.

Figure 4:
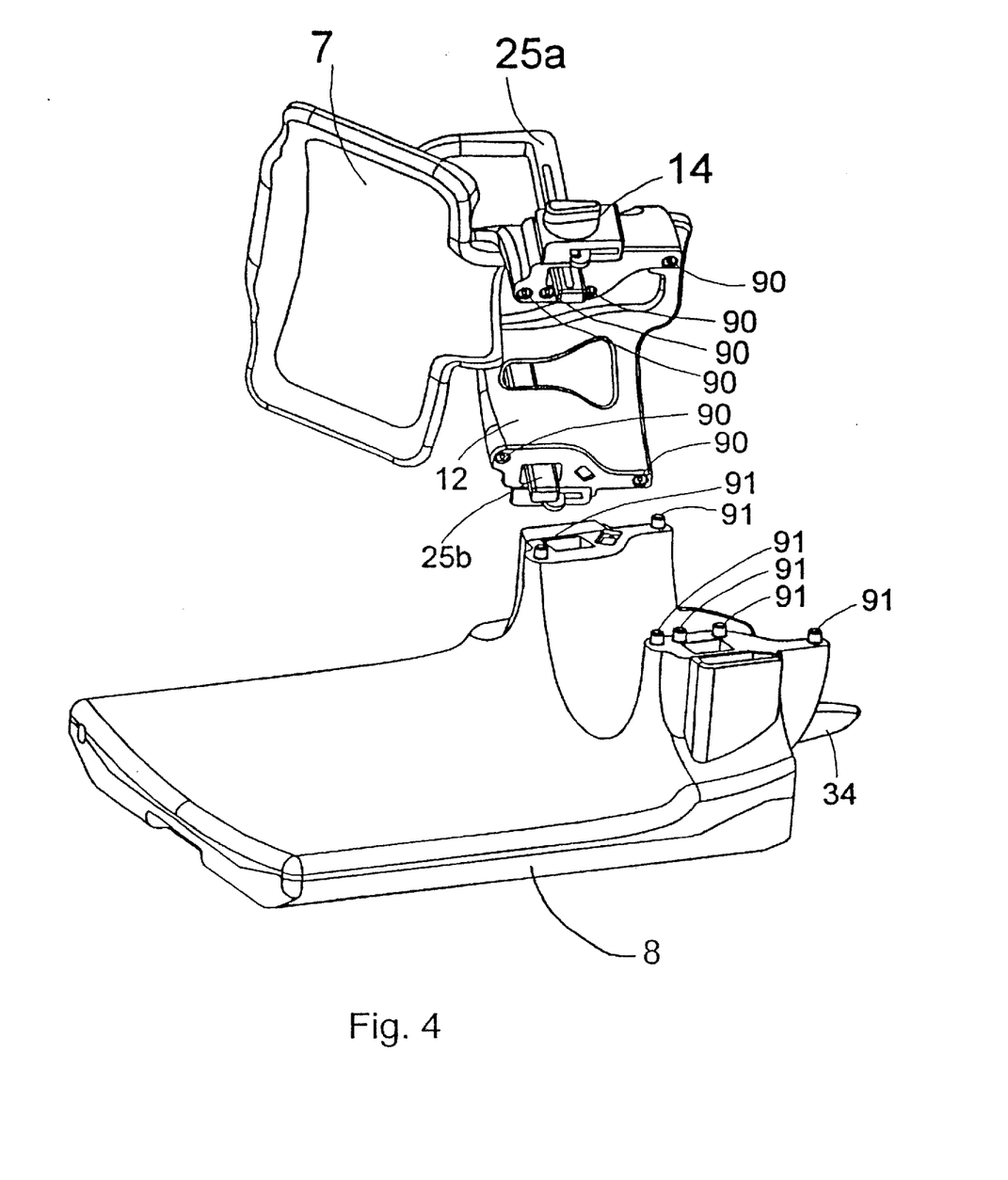
FIG. 4 is a perspective view of a split-top neck coil with attached torso coils according to the invention.
Figure 5:
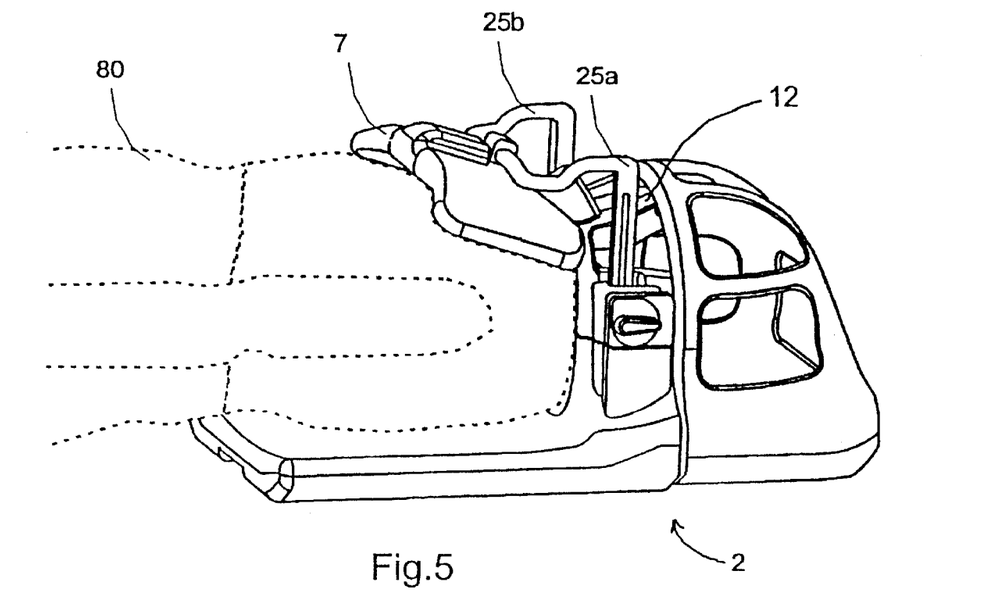
FIG. 5 is a perspective view of a system according to the invention in a operating position typical for a large patient.

Referring to FIG. 4, male electrical connectors 90 in the anterior neck coil 12 mate with female electrical connectors in the posterior neck coil 13. The anterior torso coil 7 may be attached to the anterior neck coil 12 with a pair of adjustable arms 25a, 25b as a part of a split-top anterior neck-torso coil 26 (see FIG. 2). The anterior torso coil 7 can be moved up and down in the vertical direction using the adjustable arms 25a, 25b. The adjustable arms 25a, 25b can be locked in multiple positions to hold the anterior torso coil just above the chest of the patient 80. A sliding-joint 27 allows the anterior torso coil 7 to be adjusted in the superior-inferior (i.e., head-toe) direction as well as to be tilted at an angle (e.g., approximately 0 to 30 degrees). The traveling distance, in the superior-inferior direction, of the anterior torso coil 7 is designed to be enough to allow the anterior torso coil 7 to be moved clear of the anterior neck coil 12 so that the anterior torso coil 7 can be placed below (see FIG. 1) or above (see FIG. 5) the anterior neck coil 12. When imaging a large size patient (e.g., over 300 lb) the anterior torso coil 7 is placed above the anterior neck coil 12, as shown in FIG. 5. For the smaller major patient population, the anterior torso coil 7 is placed under the anterior neck coil 12, as shown in FIG. 1.

In this embodiment, there are ten windows/openings (reference numerals 15 through 24), including the opening 16 in the head-neck section 3 for the eyes of the patient 80, i.e., an open design.

Figure 6:
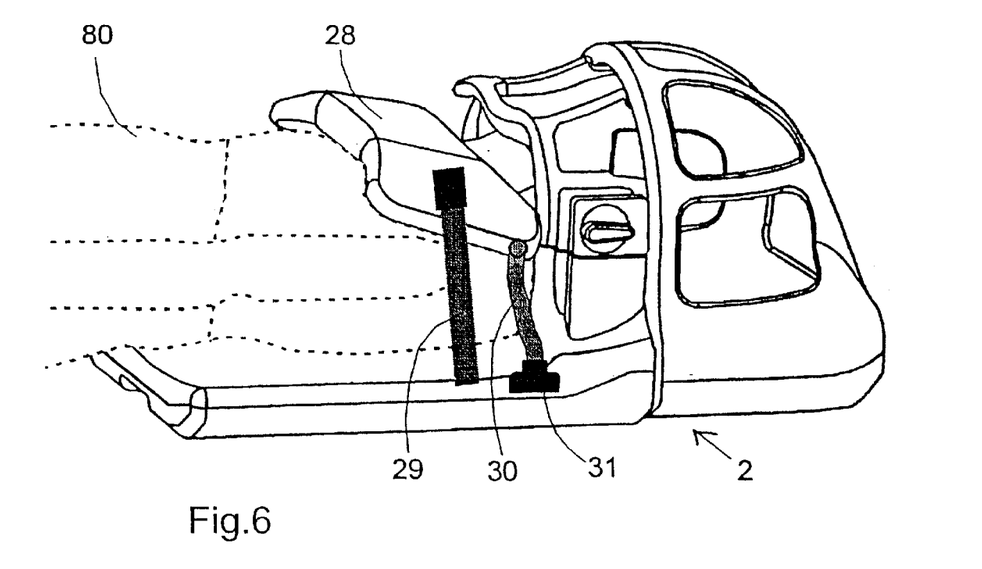
FIG. 6 is a perspective view of an additional embodiment of a system according to the invention.

Referring to FIG. 6, an alternative embodiment of an anterior torso coil 28 is substituted for the coil 7 described above. The anterior torso coil 28 is a floating type coil design, i.e., the anterior torso coil 28 is placed directly on the chest of the patient 80. In this embodiment, the anterior torso coil 28 may be, for example, secured to the posterior torso coil 8 with belts 29 (only one side shown) during imaging. The belts 29 may, for example, attach with hook and loop fasteners. The anterior torso coil 28 may be electrically connected to the circuitry of the posterior torso coil 8 via a coil cable 30 and a detachable connector 31. The anterior torso coil 28 may be removed when not being used. Similar to the anterior torso coil 7, the coil 28 can also be placed on the top of the anterior neck coil 12 when imaging a large size patient.

Referring to FIG. 2, a patient 80 may be positioned in the system 2 in the following manner. The sliding-dome head coil 5 is slid away from the split-top neck coil 6 and the anterior neck coil 12 is also moved away to allow the patient 80 to lie down on a posterior coil housing 32. The patient is cushioned by a pad 33 which serves for 1) patient comfort, 2) preventing the hair of the patient 80 from falling into the gap below a head-rest 34 and 3) reducing the movement of the head of the patient 80 during imaging. After the patient 80 is properly positioned on the posterior coil housing 32, the anterior neck coil 12 is connected to the posterior neck coil 13 so that the male connectors 90 of the anterior neck coil 12 properly engage into the female connectors 91 of the posterior neck coil 13 and the engagement is secured by the pair of latches 14. Then the position of the anterior torso coil 7 is adjusted (i.e., the vertical position, the superior-inferior position and the tilting angle) to keep it close to the chest of the patient 80 and also following the chest contour of the patient 80 as well. Next, the sliding-dome head coil 5 is closed by sliding the sliding-dome head coil 5 toward the split-top neck coil 6 until the latches 10a, 10b lock the sliding-dome head coil 5 in the closed position.

Figure 7:
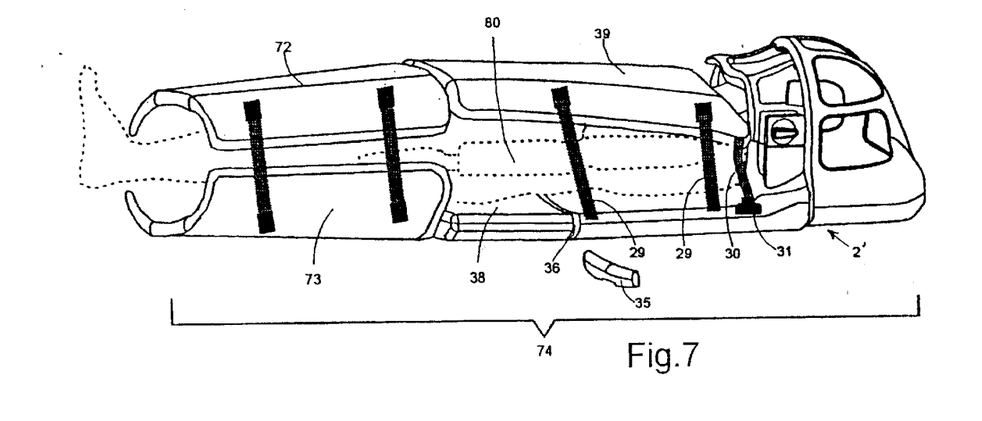
FIG. 7 is a perspective view of another embodiment of a system according to the invention.

Referring to FIG. 7, in an additional embodiment of the system 2', the posterior torso coil 8 may be provided with a connector panel 36 at the end of the posterior torso coil 8 that is normally covered by a cover 35 that may be removed to provide access to the connector panel 36. An additional coil section 38 may then be attached to the posterior torso coil 8 to extend the coverage of the system 2 to the thoracic and lumber spine. A similar design can also be implemented for an anterior torso coil, i.e., replace the short anterior torso coil 7 or coil 28 with a longer anterior torso coil 39, to extend the vascular imaging to the abdomen region. Furthermore, by adding another peripheral vascular (PV) array coil section, coverage may be extended to the vascular imaging of the low extremities.

Figure 8:
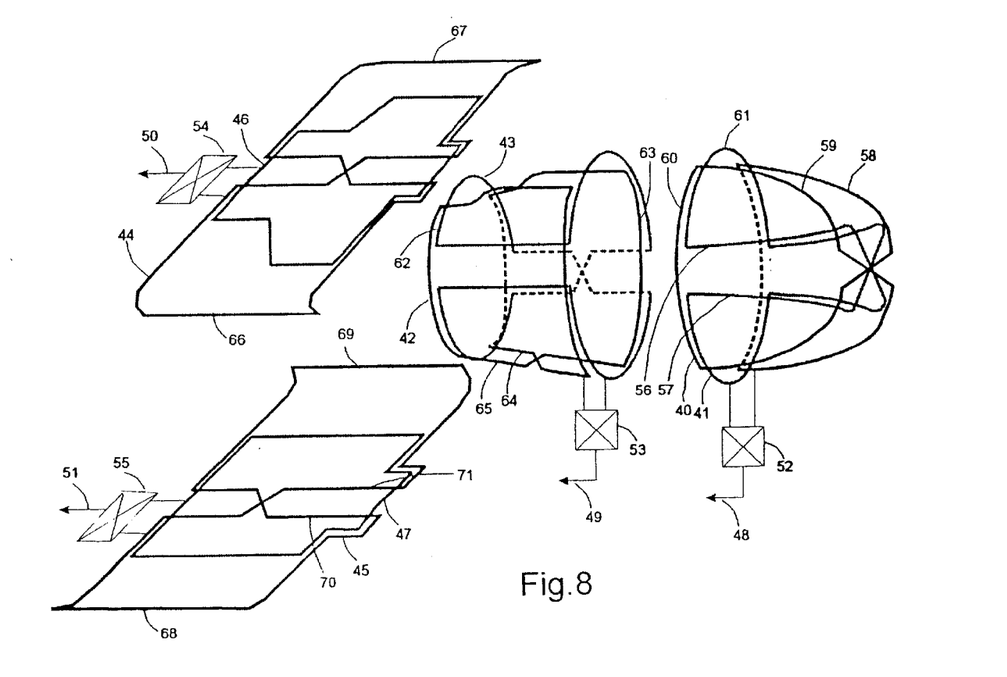
FIG. 8 is a schematic diagram of the electrical characteristics of a system according to the invention.

Referring to FIG. 8, the electrical arrangement of the system 2 includes, for example, eight linear coils, including six saddle coils 40, 41, 42, 43, 44, 45 and two loop coils 46, 47. The eight linear coils form four quadrature coil pairs: one quadrature coil pair, coils 40, 41 for the head, another quadrature coil pair, coils 42, 43 for the neck, the third quadrature coil pair, coils 46, 44 for the anterior torso and the fourth quadrature coil pair, coils 47, 45 for the posterior torso. The eight coils 40, 41, 42, 43, 44, 45, 46, 47 can be used either as eight individual channels or as four quadrature channels 48, 49, 50, 51 by combining each of the four quadrature coil pairs through a quadrature (i.e., 90 degree) combiner 52, 53, 54, 55, respectively. For head imaging, both the head channel 48 and the neck channel 49 are turned on to receive the MRI signal. To image the neck, the neck channel 49 and the anterior torso channel 50 and the posterior torso channel 51 are used. The neck channel 49 and the posterior torso channel 51 are the choice for c-spine imaging. MRA of the blood vessels from the circle of Willis to the aortic arch uses the head channel 48, the neck channel 49, the anterior torso channel 50 and the posterior torso channel 51. When a channel is not being used, it may be turned off using unshown active RF blocking circuitry (i.e., active decoupling chokes) or in the case of the floating type anterior torso coil 28, the anterior torso coil 28 may be removed when not being used.

Figure 9:
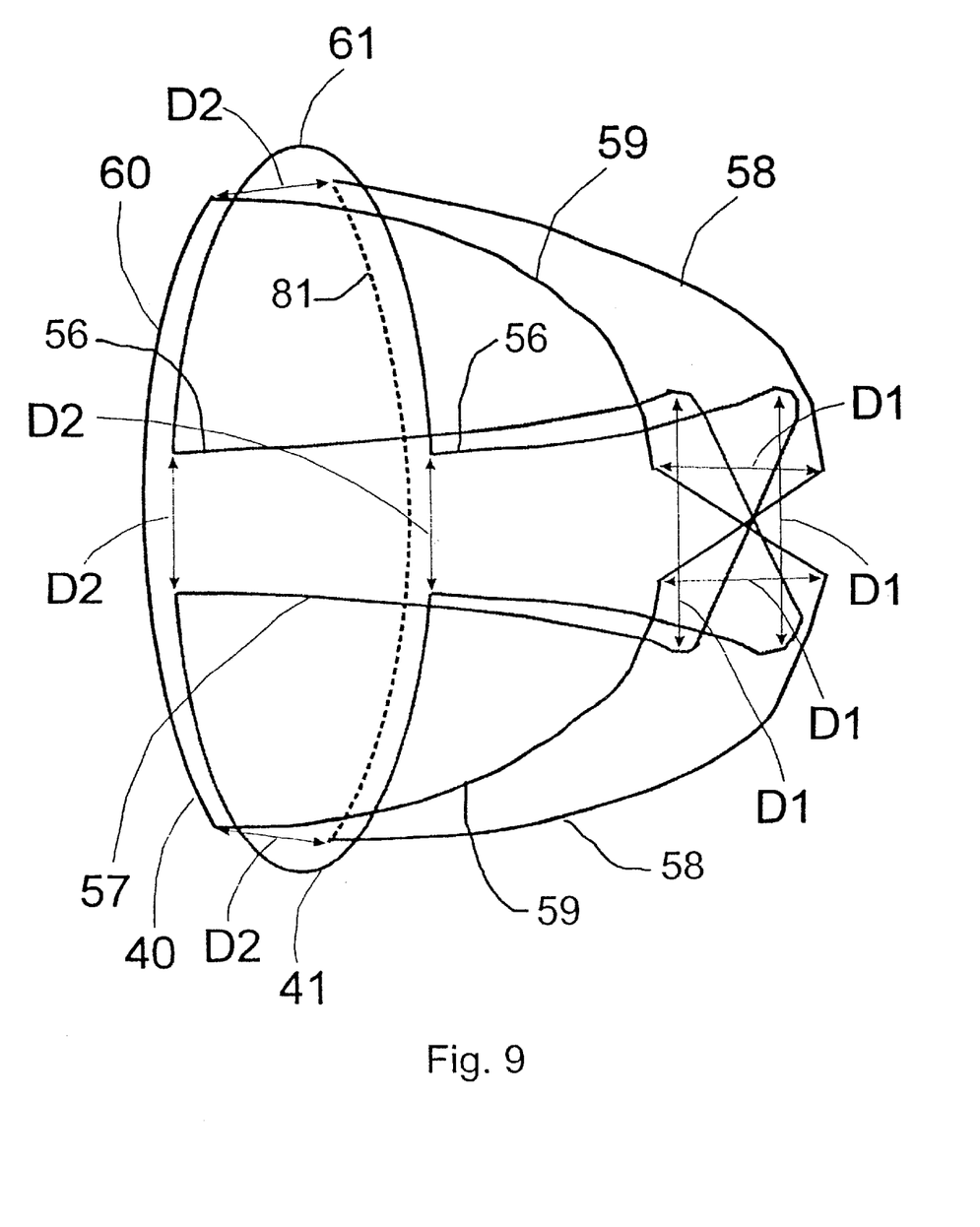
FIG. 9 is an enlarged view of the schematic diagram of the head coil portion of a system according to the invention.

Referring to FIG. 9, the saddle coils 40, 41 may each be of similar or identical volume and perpendicularly oriented to each other to form the sliding-dome head coil 5 in the form of a dome-shaped cap. It may also be desirable to shape each of the saddle coils 40, 41 such that the distance D1 between pairs of returning conductor segments (segments 56, 57 and segments 58, 59) gradually reduces to D2 as the segments reach the endrings 41, 61 and the endrings 40, 81, respectively, such that D2 is a fraction of D1. The fraction being, for example, between 0.60 and 0.85, with 0.75 being most desirable.

Referring to FIG. 8, the saddle coils 42, 43 may each be of similar or identical volume and perpendicularly oriented to each other to form the split-top neck coil 6. A similar design as that used for the head coil is also applied to the saddle coils 42, 43 for manipulating their shape: the diameter of the endring 62 at the neck region is smaller than the endring 63 at the head region. The diameter of the neck endring 62 may be for example, 10 to 30 percent less than the diameter of the endring 63 at the head region, with 20 percent being most desirable.

In addition, the separation between the pairs of returning conductors 64, 65 underneath the neck of the patient may be arranged to obtain good SNR for c-spine imaging.

The saddle coil 44 may be a semi-volume type saddle coil and the loop coil 46 a surface type loop coil to form the superior torso coil 7. For the loop coil 46, the size of its superior portion, i.e., the portion close to the neck, may be enlarged so that it can provide better coverage for the neck. The left and right wings 66, 67 of the saddle coil 44 may be bent downward so that the penetration of the saddle coil 44 is improved. Furthermore, the shape of the anterior torso coil 12 at the neck region may be optimized for purposes of providing critical coupling between the neck coils and the anterior torso coils and covering more neck volume as well.

Similarly, the saddle coil 45 may be a semi-volume type saddle coil and loop coil 47 a surface type loop coil to form the posterior torso coil 8. The shape of the posterior torso coil 8 at the neck region is also optimized for providing critical coupling between the neck and the posterior torso coils and covering more neck volume as well. The shape of the wings 68, 69 of the saddle coil 45 are gradually curved upward as the wings reach out so that the posterior saddle coil can cover deeper into the torso volume. The separation between the pair of the returning conductors 70, 71 underneath the back of the patient is arranged to obtain good SNR for the spine imaging.

The size and the shape of the anterior and posterior torso coils are carefully manipulated so that these coils can cover deep into the torso volume but not cause isolation problem between the anterior and posterior torso coils.

The direction of the magnetic field (i.e., $B_1$ field) generated by each of the eight coils is either horizontal or vertical. The inductive isolation between two quadrature coils can easily reach −25 dB or better, including the situation for each pair of quadrature coils. The inductive coupling between two in-phase (i.e., the two $B_1$ fields are in same direction) neighboring coils are minimized by the critical coupling of the two coils. The anterior torso coils reach their best critical coupling position with the neck coils when they are moved to the most superior position. Moving the anterior torso coil toward the inferior direction and tilting the anterior torso coil can only have minor effect on the isolation between the anterior torso coil and the neck coil.

The system 2 of the present invention is more patient friendly. The open design results in less claustrophobia. The smaller anterior neck coil housing, when moving toward a patient, causes less anxiety and is less threatening. The ability to place the anterior torso coil on top of the anterior neck coil allows the imaging of large patients up to 99 percentile of the patient population.

The quadrature dome head coils and the neck coils provide superior SNR for the head (30% higher as compared to a commercial quadrature head coil) and neck (20% higher as compared to a commercial quadrature neck coil) imaging and good homogeneity as well. The image quality obtained with the quadrature array coil system of the present invention for the cervical and thoracic spine is comparable to that obtained with a commercial quadrature multiple channel CTL coil. The quadrature anterior and posterior coils gain 20% higher SNR at the center of the torso volume compared to a pair of linear anterior and posterior loop coils. The image homogeneity for a large field-of-view (i.e., 48 cm) of the quadrature array coil system of the present invention is much better than that of the prior art.

In addition, the single mode quadrature array coil design makes the inductive decoupling between two neighboring coils easier and simpler.

The present invention provides a multiple channel RF quadrature combination array coil system that can be used as a head-only coil, a neck-only coil, a spine-only coil and also a large field-of-view (48 cm from the circle of Willis to the aortic arch) vascular coil in a single integrated system.

We claim:

1. An MRI array coil system for neurovascular and spine imaging of a human, said system comprising:
    a neck coil having a split top;
    a head coil having a dome region, said head coil being slidable between a closed position adjacent to said neck coil and an open position spaced away from said neck coil;
    a posterior torso coil attached to said neck coil; and
    an anterior torso coil adapted to cooperate with said posterior coil,
    wherein said anterior torso coil is adjustably attached to said split top.

2. A system according to claim 1, wherein said anterior torso coil may be placed above or below said split top.

3. An MRI array coil system for neurovascular and spine imaging of a human, said system comprising:
    a neck coil having a split top;
    a head coil having a dome region, said head coil being slidable between a closed position adjacent to said neck coil and an open position spaced away from said neck coil;
    a posterior torso coil attached to said neck coil; and
    an anterior torso coil adapted to cooperate with said posterior coil,
    wherein said anterior torso coil is a floating type coil.

4. An MRI array coil system for neurovascular and spine imaging of a human, said system comprising:
    a neck coil having a split top;
    a head coil having a dome region, said head coil being slidable between a closed position adjacent to said neck coil and an open position spaced away from said neck coil;
    a posterior torso coil attached to said neck coil; and
    an anterior torso coil adapted to cooperate with said posterior coil,
    wherein:
    the head coil is formed by a quadrature pair of saddle coils
    each having returning conductor segments, dome top region and endrings, the separation of respective pairs of conductor segments gradually reducing by a factor of between about 0.6 and 0.85 from the top of the dome region to the head coil endrings;
    the neck coil is formed by a quadrature pair of saddle coils each having an endring at a neck region and at a head region, the diameter of neck region endring being a percentage between about 10 percent and 20 percent smaller than the diameter of the head endring;

the anterior torso coil is formed by a quadrature pair of coils including a loop coil and a saddle coil; and
the posterior torso coil is formed by a quadrature pair of coils including a loop coil and a saddle coil.

5. A system according to claim 4, wherein said factor is about 0.75 and said percentage is about 20 percent.